(12) United States Patent
Razavi et al.

(10) Patent No.: US 7,388,062 B2
(45) Date of Patent: Jun. 17, 2008

(54) GROUP IIIB METAL COMPLEXES WITH "CONSTRAINED GEOMETRY" FLUORENYL BASED LIGANDS

(75) Inventors: Abbas Razavi, Mons (BE); Jean-François Carpentier, Acigne (FR); Evgueni Kirillov, Erlangen (DE)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 10/548,506

(22) PCT Filed: Mar. 4, 2004

(86) PCT No.: PCT/EP2004/002378

§ 371 (c)(1),
(2), (4) Date: Jun. 16, 2006

(87) PCT Pub. No.: WO2004/078795

PCT Pub. Date: Sep. 16, 2004

(65) Prior Publication Data

US 2006/0264586 A1 Nov. 23, 2006

(30) Foreign Application Priority Data

Mar. 7, 2003 (FR) .................................. 03 02832

(51) Int. Cl.
*C08F 4/6392* (2006.01)
(52) U.S. Cl. ...................... 526/164; 526/160; 526/161; 526/165; 526/172; 502/103; 502/152; 502/167; 556/53
(58) Field of Classification Search ................ 502/103, 502/152, 155, 167; 526/134, 161, 165, 164, 526/160, 172; 556/53
See application file for complete search history.

(56) References Cited

U.S. PATENT DOCUMENTS

| | | | |
|---|---|---|---|
| 5,436,305 A | * | 7/1995 | Alt et al. ...................... 526/160 |
| 5,464,906 A | * | 11/1995 | Patton et al. ................. 525/240 |
| 6,291,655 B1 | | 9/2001 | Okuda et al. |
| 6,599,996 B1 | | 7/2003 | Okuda et al. |

* cited by examiner

*Primary Examiner*—Caixia Lu
(74) *Attorney, Agent, or Firm*—Diane Kilpatrick-Lee

(57) ABSTRACT

The present invention discloses a metallocene catalyst component based on a Group IIIb metal of the periodic Table and a bridged heteroatom-fluorenyl ligand. It also discloses its method of preparation and its use in polymerisation.

11 Claims, 8 Drawing Sheets

GROUP IIIB METAL COMPLEXES WITH "CONSTRAINED GEOMETRY" FLUORENYL BASED LIGANDS

The present invention relates to the field of "constrained geometry catalyst" systems based on Group IIIb metals of the Periodic Table. It also relates to their synthesis and their use in olefin polymerisation.

"Constrained geometry catalysts" (CGC) are half-sandwich complexes bearing hetero-bifunctional cyclopentadienyl-amido ligands. They have attracted much attention owing to several reasons:

replacing of a cyclopentadienyl moiety in linked bis(cyclopentadienyl) ligands by a less electron-donating amido group results in the formation of ansa-metallocene-like complexes with higher Lewis acidity; and therefore potentially enhanced catalytic activity towards Lewis basic substrates.

there are many more possibilities to design new catalytic geometries by selecting appropriate substituents on the cyclopentadienyl ring, on the bridging atom and on the heteroatom of the side chain.

The synthesis and polymerisation abilities of cyclopentadienyl-amido complexes of group III metals (Sc, Y, Yb, Lu) have been described for example in Shapiro et al. (P. J. Shapiro, W. D. Cotter, W. P. Schaefer, J. A. Labinger, J. E. Bercaw; in J. Am. Chem. Soc., 1994, 116, 4623.) or in Hultzsch et al. (K C. Hultzsch, P. Voth, K. Beckerle, T. P. Spaniol, J. Okuda; in Organometallics, 2000, 19, 228.), or in Tian et al. (S. Tian, V. M. Arredondo, C. L. Stern, T. J. Marks; in Organometallics, 1999, 18, 2568.), or in Mu et al. (Y. Mu, W. Piers, M.-A. MacDonald, M. J. Zaworotko; in Can. J. Chem., 1995, 73, 2233.) or in Arndt and Okuda (S. Arndt, J. Okuda, in Chem. Rev., 2002, 102, 1953.)

All these publications however were limited to lantanide compounds with combined cyclopentdienyl-amido ligands. None has addressed the field of fluorenyl-amido ligands.

It is an object of the present invention to prepare in good yield bridged half-sandwich metallocene components based on fluorenyl-heteroatom ligands and based on Group IIIb metals of the Periodic Table.

It is another aim of the present invention to prepare catalyst components efficient in the controlled polymerisation of styrene.

It is a further aim of the present invention to prepare catalyst components capable of preparing polymethylmethacrylate.

More generally, the present invention aims at preparing catalyst systems efficient in the controlled polymerisation of polar or non polar monomers.

Accordingly, the present invention discloses a metallocene catalyst component based on a Group IIIb metal of the Periodic Table and a bridged constrained geometry fluorenyl-based ligand.

In a first embodiment, the present invention discloses a metallocene catalyst component of the general formula $$[(Flu\text{-}SiR_2\text{---}N\text{---}R')M(R'')(L)_n]_m \qquad (I)$$

wherein Flu is a fluorenyl, substituted or unsubstituted, M is a Group IIIb metal of the Periodic Table, $SiR_2$ is a structural bridge between N and Flu (9-position) imparting stereorigidity to the component wherein each R is the same or different and is an alkyl having from 1 to 20 carbon atoms, R' is hydrogen or is of the form $ZR^\$_3$ wherein Z is C or Si and $R^\$$ is a hydrocarbyl having from 1 to 20 carbon, R" is hydrogen, or a hydrocarbyl having from 1 to 20 carbon atoms, said hydrocarbyl possibly containing one or more Si atoms, or is a halogen, L is a co-ordinating solvent, n is 0, 1 or 2, and m is 1 or 2.

The substituents on the fluorenyl are not particularly limited, they can be the same or different and are of the form $ZR^\$_3$ as defined here-above; they include particularly hydrocarbyls having from 1 to 20 carbon atoms. Preferably, they are located at positions 3 and 6, or at positions 4 and 5, or at positions 2 and 7 and more preferably, they are the same.

M is preferably yttrium, lanthanum or a member of the lanthanide series. Throughout this description, the term "lanthanide series" means the rare earth series of elements having atomic numbers of from 58 to 71. In the lanthanide series M is preferably neodymium, samarium. More preferably, M is yttrium.

Preferably, N is substituted and more preferably, the substituent is tert-butyl.

Preferably, R" is hydrogen or an alkyl or an aryl or an allyl or a halogen, and m is 1 when R" is an alkyl or an aryl or an allyl, m is 2 when R" is hydrogen or a halogen. When R" is a halogen, it is preferably Cl, I, or Br.

The co-ordinating solvent is typically an ether such as for example tetrahydrofuran (THF), dimethoxyether (DME) or diethyl oxide ($Et_2O$).

In order to be active in polymerization, compounds of type (I), wherein R" is a halogen must be alkylated first with an adequate reagent. Typical reagents can be selected from $LiR^*$, $R^*MgX$, $MgR^*_2$, $AlR^*_3$, $AlR^*_nX_{3-n}$, $[Li]^+[AlR^*_nX_{3-n}]^-$ a methylalumoxane (MAO), wherein $R^*$ is an alkyl, aryl or allyl having from 1 to 20 carbon atoms and X is a halogen, preferably Cl. This list should not be considered as limitative.

In a second embodiment, the present invention discloses a metallocene catalyst component of the general formula

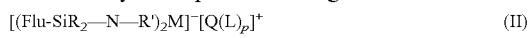

wherein all symbols are as defined in formula (I), Q is an alkali, an earth alkali or a Group IIIa metal of the Periodic Table and p is from 2 to 4.

Q is preferably Li, Na, Mg or Al.

When the ion-pair in complex II is fully dissociated, p is 4 and when the ion-pair is partially associated, p is 2 or 3.

The present invention discloses a first method, based on a salt metathesis reaction method for preparing the catalyst components (I) or (II) that comprises the steps of:

a) suspending $MX_3(THF)_n$ in an ether;
b) suspending a deprotonated dilithium salt [Flu-SiR$_2$—N—R']Li$_2$ in the same or another ether;
c) carrying out the salt metathesis reaction of suspensions a) and b) at a temperature of from −80° C. to 60° C.
d) recrystallising the crude product obtained in c) after evaporation of volatiles from an ether or a mixture of an ether and an hydrocarbon at a temperature of from −60° to −0° C.;
e) retrieving a crystalline powder of formula (I) or (II)

In another embodiment of the present invention, complex (I) wherein R" is a halogen, can comprise the additional step of alkylation with an alkylating agent to give complex (I) wherein R" is a hydrocarbyl as defined above.

Suitable alkylating agent can be selected from $LiR^+$, $R^+MgX$, $MgR^+_2$, $AlR^+_3$, $AlR^+_nX_{3-n}$ and $[Li]^+[AlR^+_nX_{3-n}]^-$ wherein $R^+$ is an alkyl, an aryl or an allyl having from 1 to 20 carbon atoms and X is a halogen, preferably Cl.

The present invention discloses a second method, based on an alkane elimination reaction, for preparing specifically the catalyst component

wherein R" is specifically a hydrocarbyl having from 1 to 20 carbon atoms, said hydrocarbyl possibly containing one or more Si atoms, that comprises the steps of reacting the triscarbyl complex $M(R")_3(L)_n$, either presynthesised or generated in situ, with one equivalent of the diproteo ligand (FluH—SiR$_2$—NH—R').

The triscarbyl complex $M(R")_3(L)_n$ is preferably generated in situ as the reaction product of $MCl_3(THF)_n$ and 3 equivalents of LiR". The reaction temperature for the preparation of complex (I) is of from 0° C. up to 75° C. and preferably of from 40 to 50° C. For the second method of preparation described here-above, M is preferably Yttrium and the bridge SiR$_2$, is preferably a dialkyl silyl.

These two methods can comprise the additional step of hydrogenolising carbyl complex (I) to prepare complex $$[(Flu\text{-}SiR_2\text{—}N\text{—}R')M(H)(L)_n]_m \tag{I'}$$

Suitable hydrogenolising agents can be selected from dihydrogen or an hydrosilane, e.g. phenylsilane. The reaction is preferably carried out at room temperature at about 25° C. and at atmospheric pressure in an hydrocarbon solvent, e.g. benzene or toluene. The reaction product is insoluble in both polar (ethers) and non-polar (hydrocarbons) solvents.

The present invention further discloses a catalyst system based upon any one or more of catalyst components of formulas (I) and/or (II) and a suitable activating agent and/or a transfer agent.

The present invention discloses a process for polymerisation comprising the steps of:
a) introducing a catalyst system based on any one or more of catalyst components of formulas (I) and/or (II) in the reactor,
b) optionally introducing an activating agent or a transfer agent in the reactor,
c) feeding a monomer and an optional comonomer,
d) maintaining the system under polymerisation conditions,
e) retrieving the desired polymer.

The optional activating agent includes Lewis acids having an ionising action and having a low or no co-ordinating capability. Typically, all the activators used with the metals Group IV of the Periodic Table can be used in the present invention. Suitable aluminium-containing activating agents comprise an alumoxane an aluminium alkyl or an alkylaluminate $[Li]^+[AlR*_nX_{3-n}]^-$ The alumoxanes that can be used in the present invention are well known and preferably comprise oligomeric linear and/or cyclic alkyl alumoxanes represented by the formula (III):

for oligomeric linear alumoxanes; and formula (IV)

for oligomeric cyclic alumoxanes, wherein n is 1-40, preferably 10-20; m is 3-40, preferably 3-20; and R is a $C_1$-$C_8$ alkyl group, preferably methyl. Generally, in the preparation of alumoxanes from, for example, aluminium trimethyl and water, a mixture of linear and cyclic compounds is obtained.

Suitable boron-containing activating agents may comprise a triphenylcarbenium boronate, such as tetrakis-pentafluorophenyl-borato-triphenylcarbenium as described in EP-A-0427696:

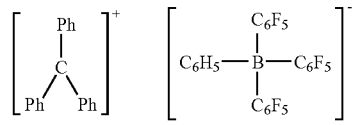

or those of the general formula below, as described in EP-A-0277004 (page 6, line 30 to page 7, line 7):

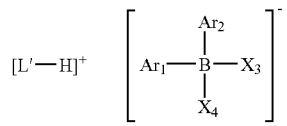

Other preferred activating agents include hydroxy isobutylaluminium and a metal aluminoxinate.

Alkylating agents of the type $MgR^=_2$ can also be used as activating agents, wherein each $R^=$ is the same or different and is a hydrocarbyl having from 1 to 20 carbon atoms, and optionally containing one or more Si atoms The transfer agents comprise for example $H_2$ and hydrosilanes of the formula $HSiR'''_3$ wherein each R''' is the same or different and is either an H atom or a hydrocarbyl having from 1 to 20 carbon atoms. They are selected in accordance with the monomer to be polymerised.

The monomers that can be used in the present invention include non polar monomers such as for example ethylene, alpha-olefins, styrene and polar monomers such as for example (meth)acrylates or dienes. Preferably, styrene and methyl methacrylate have been used.

The catalyst system of the present invention may be employed in any type of homo- or co-polymerisation method, provided that the required catalytic activity is not impaired. In a preferred embodiment of the present invention, the catalyst system is employed in a bulk polymerisation process or in a solution polymerisation process, which is homogeneous, or in a slurry process, which is heterogeneous. In a solution process, typical solvents include THF or hydrocarbons having from 4 to 7 carbon atoms such as heptane, toluene or cyclohexane. In a slurry process, it is necessary to immobilise the catalyst system on an inert support, particularly a porous solid support such as talc, inorganic oxides and resinous support materials such as polyolefin. Preferably, the support material is an inorganic oxide in its finely divided form.

Suitable inorganic oxide materials that are desirably employed in accordance with this invention include group IIA, IIIA, IVA, or IVB metal oxides such as silica, alumina and mixtures thereof. Other inorganic oxides that may be employed, either alone or in combination with the silica or alumina, are magnesia, titania, zirconia, and the like. Other suitable support materials, however, can be employed, for example, finely divided functionalised polyolefins such as finely divided polyethylene.

Preferably, the support is a silica support having a surface area of from 200-700 $m^2/g$ and a pore volume of from 0.5-3 ml/g.

The polymerisation temperatures range from –20° C. up to 100° C.

The present invention also covers the polymers obtainable by polymerisation in the presence of the catalysts components described hereabove.

LIST OF FIGURES

EXAMPLES

Synthesis of [3,6-di-*t*Bu-$C_{13}H_6$—$SiMe_2$-N*t*Bu]Y($CH_2SiMe_3$)(THF)$_2$ (1)

(a) NMR scale reaction: An NMR tube equipped with a teflon valve was charged with Y[$CH_2SiMe_3$]$_3$(THF)$_2$ (32.4 mg, 0.065 mmol) and 3,6-di-*t*Bu-$C_{13}H_6$H—$SiMe_2$-NH*t*Bu (26.7 mg, 0.065 mmol) and benzene-$d_6$ (~0.6 mL) was condensed in at −196° C. The tube was stopped with valve and heated to room temperature. Progress of the reaction was monitored periodically by $^1$H NMR spectroscopy.

Figure 2:
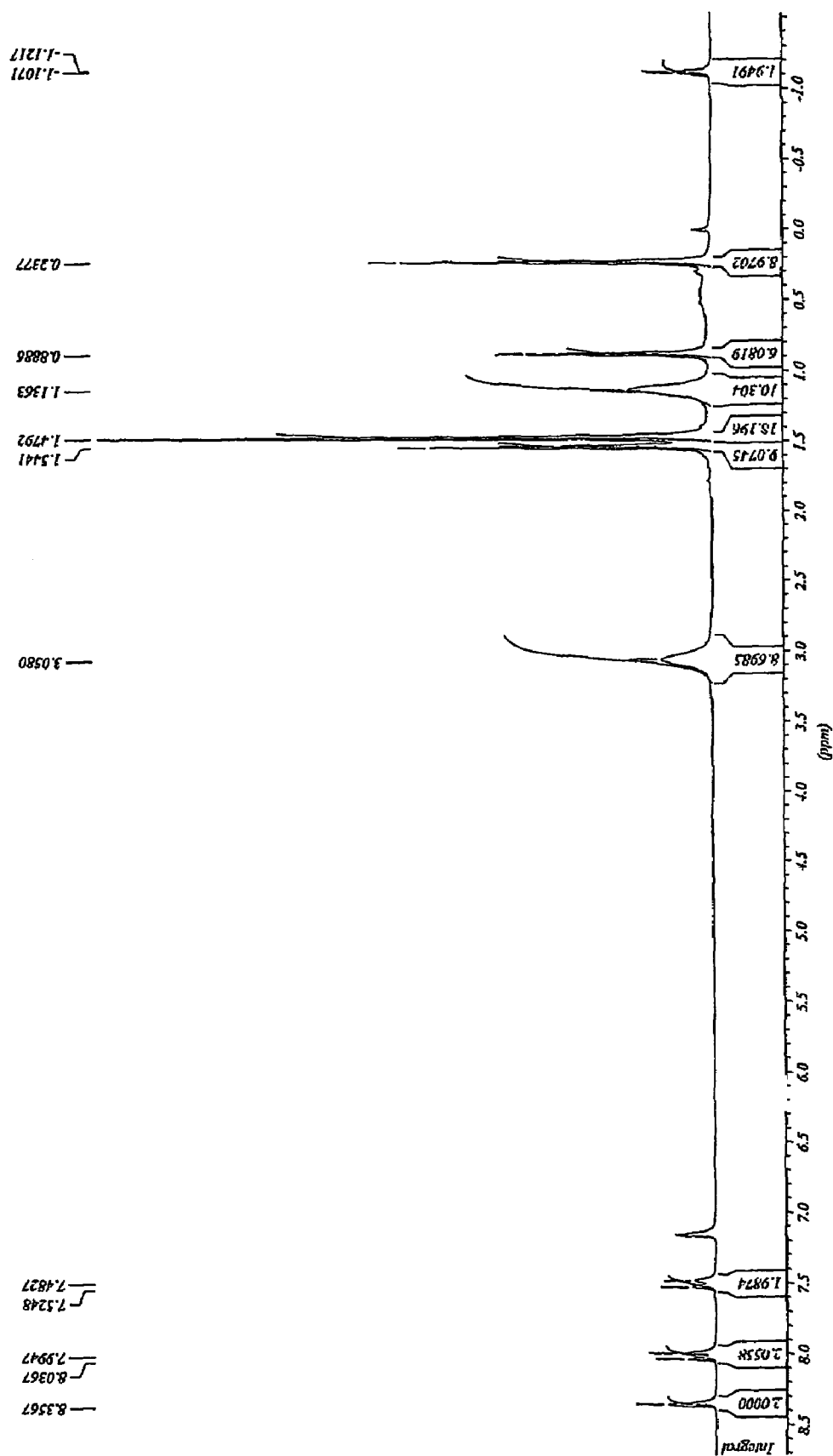
FIG. 2 represents the $^1$H NMR spectrum of complex[3,6-di-*t*Bu-$C_{13}H_6$—$SiMe_2$-N*t*Bu]Y($CH_2SiMe_3$)(THF)$_2$ (1) in $C_6D_6$ at 25° C.
Figure 3:
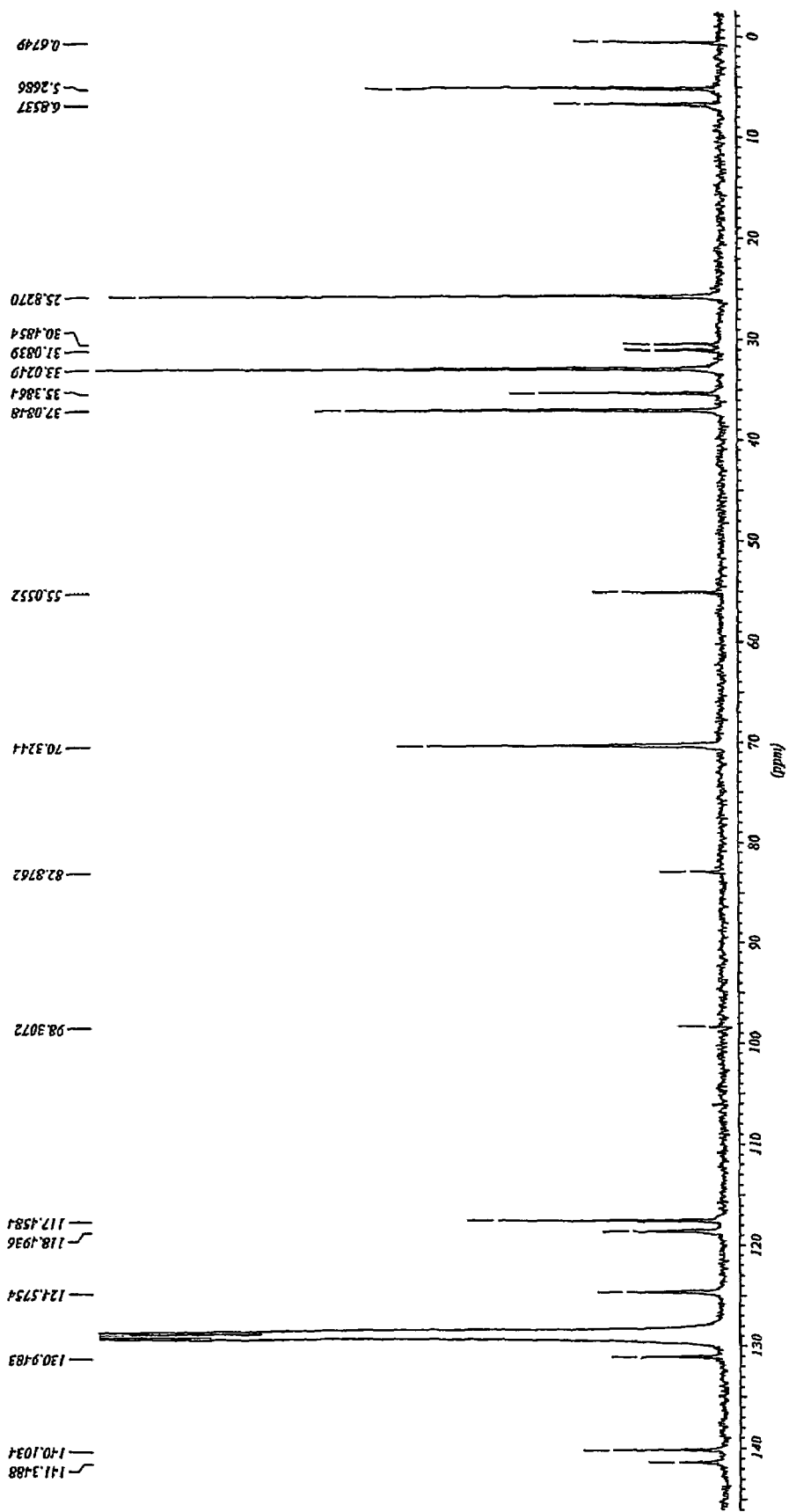
FIG. 3 represents the $^{13}$C NMR spectrum of complex ([3,6-di-*t*Bu-$C_{13}H_6$—$SiMe_2$-N*t*Bu]Y($CH_2SiMe_3$)(THF)$_2$ (1) in $C_6D_6$ at 25° C.
Figure 4:
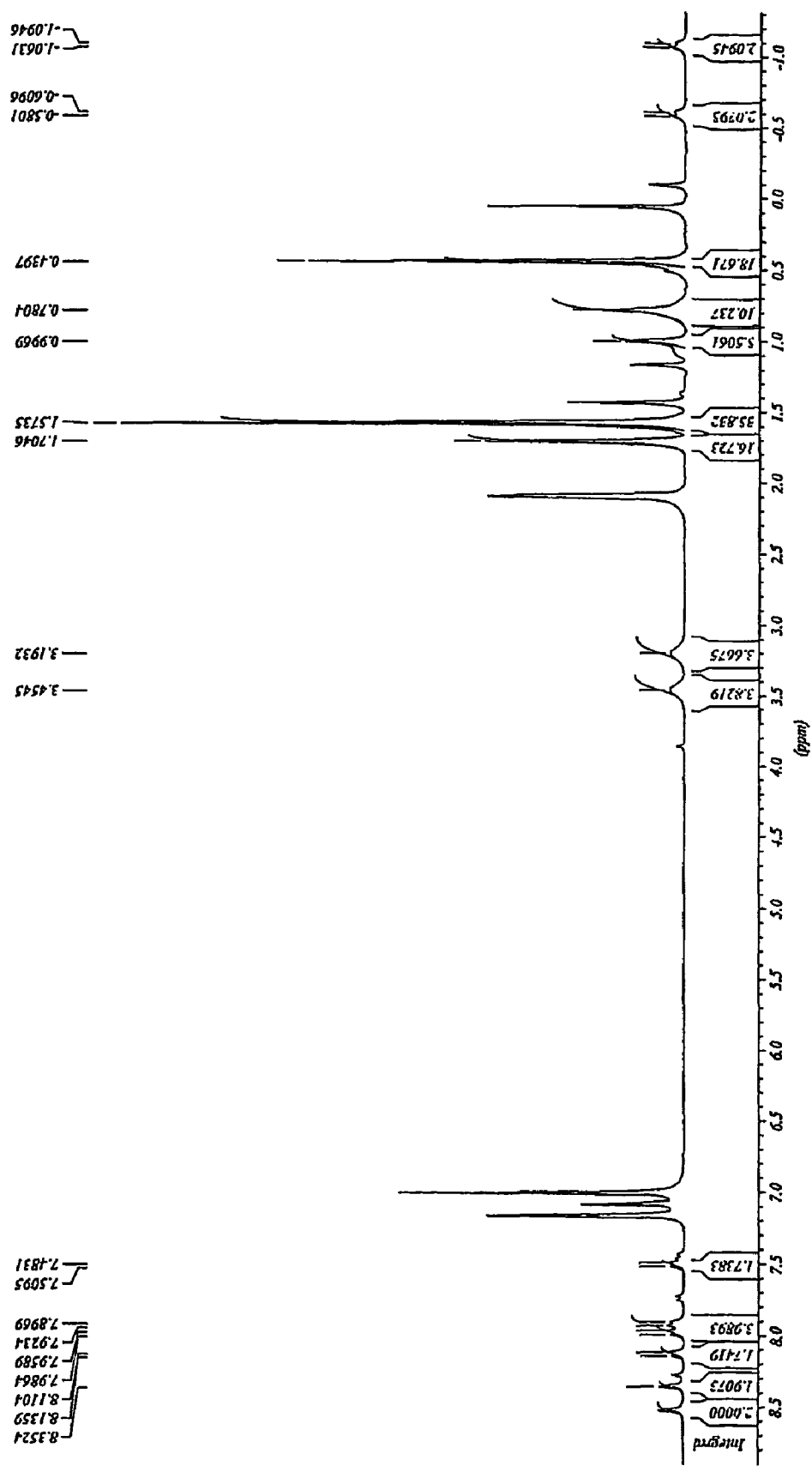
FIG. 4 represents the $^1$H NMR spectrum of complex [3,6-di-*t*Bu-$C_{13}H_6$—$SiMe_2$-N*t*Bu]Y($CH_2SiMe_3$)(THF)$_2$ (1) in $C_6D_6$ at −70° C.

(b) Preparative scale reaction: Anhydrous YCl$_3$ (338 mg, 1.73 mmol) was slurried in THF (15 mL) and stirred at 80° C. for 1 h. The solvent was removed in vacuo and the solid residue was suspended in pentane (20 mL). The suspension was cooled to −78° C., a solution of LiCH$_2$SiMe$_3$ (5.2 mL of a 1M solution in pentane, 5.2 mmol) was added, and the suspension was stirred at 0° C. for 2 h. The suspension was filtered and the white solid was extracted with pentane (2×10 mL). LiCl was filtered off and a solution of 3,6-di-*t*Bu-$C_{13}H_6$H—$SiMe_2$-NH*t*Bu (578 mg, 1.42 mmol) in pentane (30 mL) was added at 0° C. The reaction mixture was warmed to room temperature and stirred for 30 h. The solution was filtered and concentrated in vacuo. The crude product was [$C_{13}H_6$—$SiMe_2$-N*t*Bu]Y($CH_2SiMe_3$)(THF)$_2$ (1) (0.63 g, 68%). The $^1$H NMR spectrum of complex (1) is represented in FIG. 2 and gave the following results: (benzene-$d_6$, 200 MHz, 25° C.): δ 8.34 (d, 2H, $^4J_{HH}$=2.0 Hz, 4,5-H), 7.97 (d, 2H, $^3J_{HH}$=8.3 Hz, 1,8-H), 7.57 (dd, 2H, $J_{HH}$=2.0, 8.3 Hz, 2,7-H), 3.0 (m, 8H, α-$CH_2$, THF) 1.61 (s, 9H, NCCH$_3$), 1.50 (s, 18H, CCH$_3$(Flu)), 1.17 (m, 8H, β-$CH_2$, THF), 0.78 (s, 6H, SiCH$_3$), 0.00 (s, 9H, $CH_2SiCH_3$), −0.89 (d, $J_{YH}$=3.3 Hz, 2H, YCH$_2$). The $^{13}$C NMR of complex (1) is represented in FIG. 3 and gave the following results. (benzene-$d_6$, 75 MHz, 25° C.): δ 140.7, 139.4, 130.3, 123.9, 117.8, 116.7, 115.5 (C-1, -2, -3, -4, -5, -6, -7, -8), 82.2 (C-9), 69.7 (α-THF), 54.3 (NCCH$_3$), 36.4 (NCCH$_3$), 34.7 (Flu-CCH$_3$), 32.3 (Flu-CCH$_3$), 30.2 (d, $^1J(Y, C)$=45.2 Hz, YCH$_2$), 25.1 (β-THF), 6.2 (SiCH$_3$), 4.6 ($CH_2SiCH_3$). The $^1$H NMR spectrum of complex (1) (benzene-$d_6$, 200 MHz, −70° C.) is represented in FIG. 3. The NMR spectroscopy thus indicates that on the NMR time scale, complex (1) is symmetric in benzene at 25° C., but appears dissymmetric at a temperature lower than −30° C.

Figure 1:
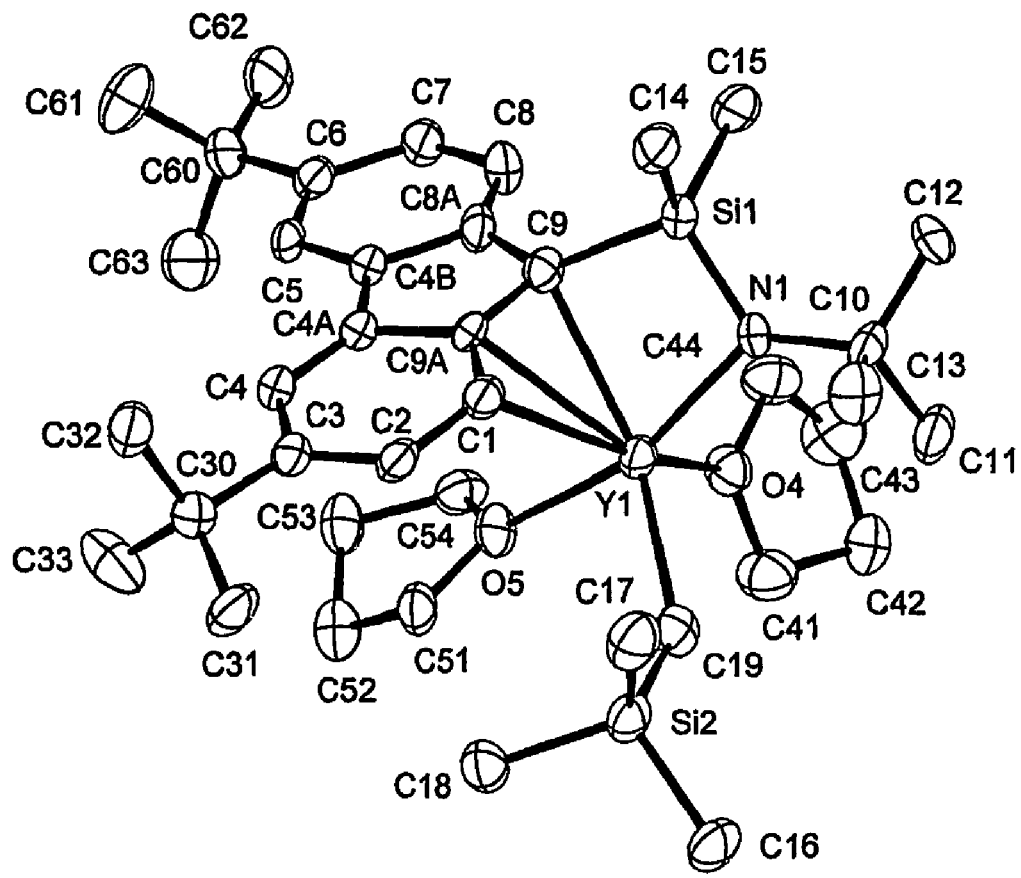
FIG. 1 represents the crystal structure of the molecule [3,6-di-*t*Bu-$C_{13}H_6$—$SiMe_2$-N*t*Bu]Y($CH_2SiMe_3$)(THF)$_2$ (1).

An X-ray diffraction study of monocrystals of complex (1) revealed that the fluorenyl moiety is bonded via an unusual exocyclic $\eta^3$-fashion, which involves the bridgehead carbon atom of the central ring (C(9A)) and the two adjacent carbon atoms of one six-membered ring (C(9), C(1)), wherein the carbon atoms are numbered as displayed in FIG. 1, which represents the structure of molecule (1). There are two THF molecules coordinated per metal atom in molecule (1) as compared with 14-electron mono-solvated [$\eta^5$: $\eta^1$-$C_5Me_4$-$SiMe_2$-N*t*Bu]Y($CH_2SiMe_3$)(THF) complex described by Hultzsch et al. (K. C. Hultzsch, P. Voth, K. Beckerle, T. P. Spaniol, J. Okuda; in Organometallics, 2000, 19, 228.). Also, molecule (1) can be considered formally as a 14-electron complex and coordination number of the yttrium atom is 6. Both coordinated THF ligands are not equivalent according to X-ray data; the difference between the two Y—O distances is 0.05 Å, suggesting that one THF molecule could be involved in dissociative processes.

Salt Metathesis Reaction between [3,6-di-*t*Bu-$C_{13}H_6$—$SiMe_2$-N*t*Bu]Li$_2$ and YCl$_3$(THF)$_n$. Preparation of [{(*t*Bu$_2$-$C_{13}H_6$)—$SiMe_2$-N*t*Bu}$_2$Y]$^-$[Li(THF)$_4$]$^+$(2).

Figure 5:
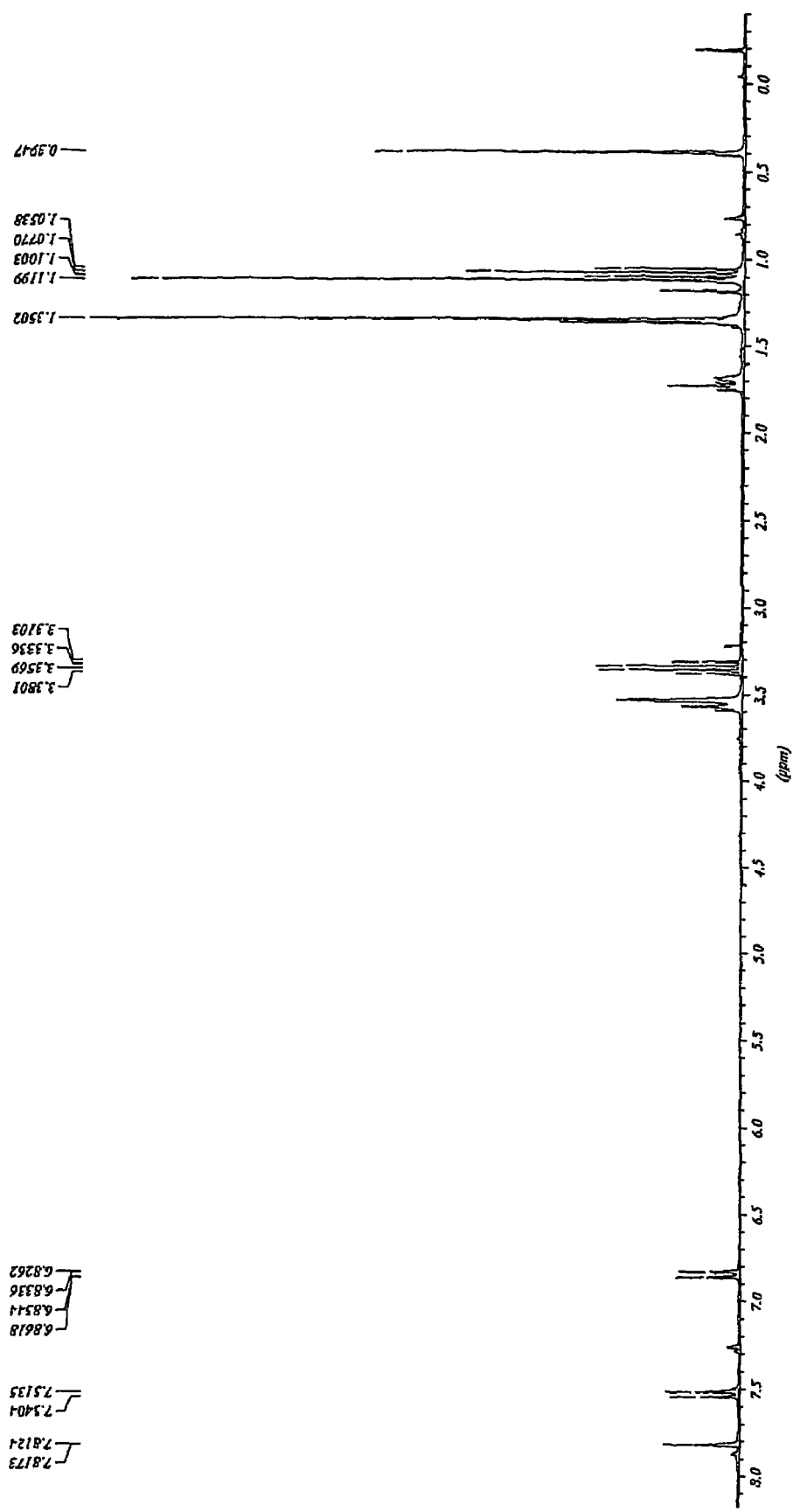
FIG. 5 represents the $^1$H NMR spectrum of complex [{(*t*Bu$_2$-$C_{13}H_6$)—$SiMe_2$-N*t*Bu}$_2$Y]$^-$[Li(THF)$_4$]$^+$ (2) in THF-$d_8$ at 25° C.
Figure 6:
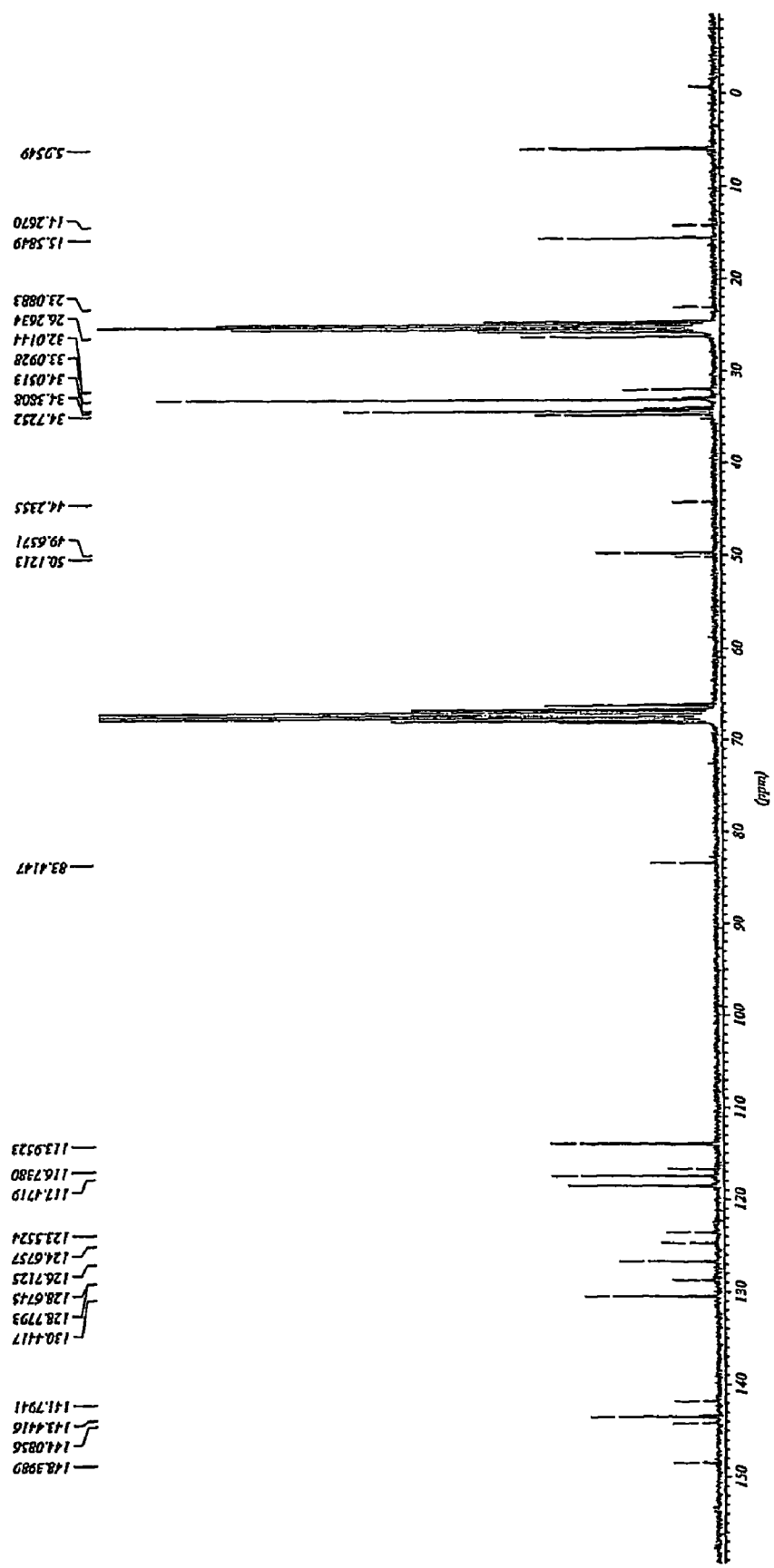
FIG. 6 represents the $^{13}$C NMR spectrum of complex [{(*t*Bu$_2$-$C_{13}H_6$)—$SiMe_2$-N*t*Bu}$_2$Y]$^-$[Li(THF)$_4$]$^+$ (2) in THF-$d_8$ at 25° C.
Figure 7:
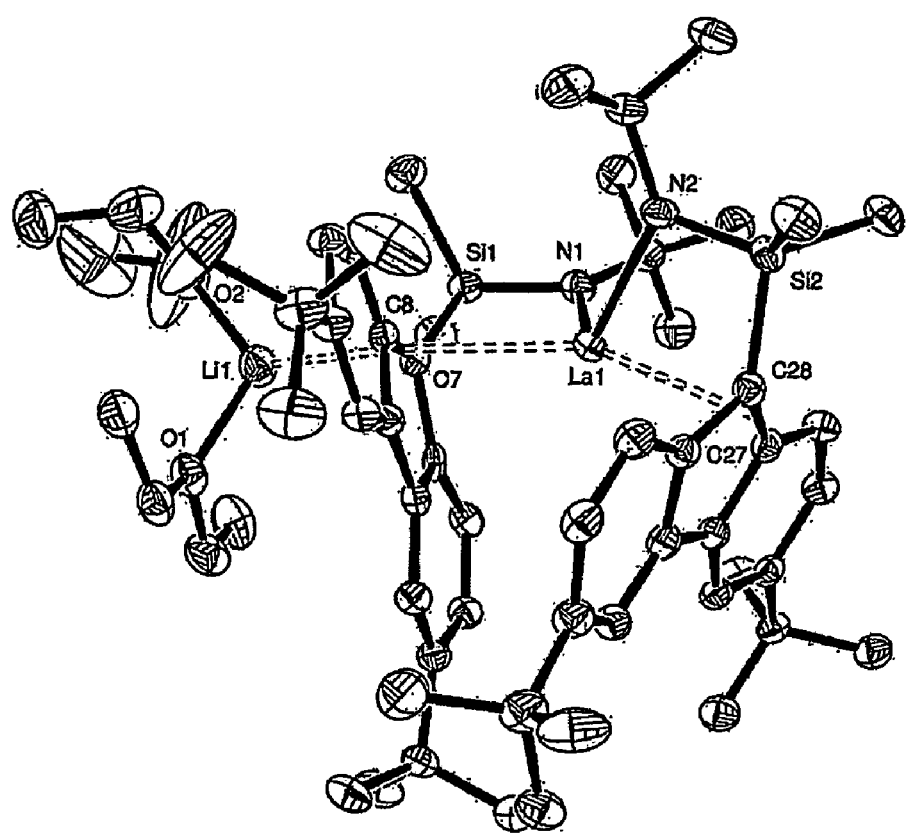
FIG. 7 represents the crystal structure of the molecule [{3,6-di-*t*Bu-$C_{13}H_6$—$SiMe_2$-N*t*Bu}$_2$La]$^-$[Li(OEt$_2$)$_2$]$^+$ (4)
Figure 8:
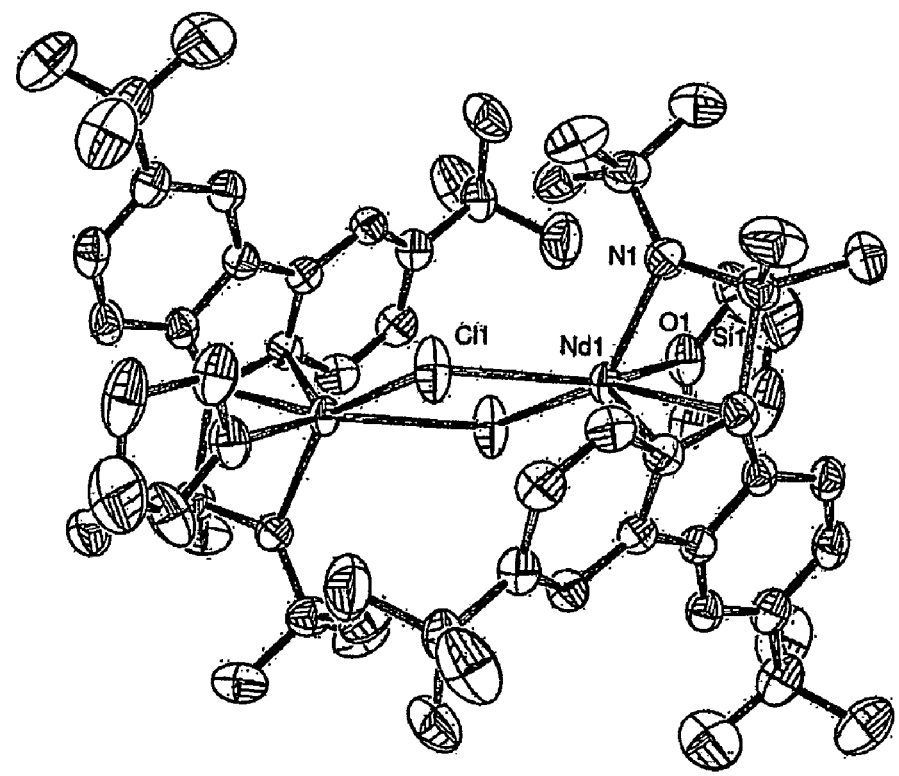
FIG. 8 represents the crystal structure of the molecule [(3,6-di-*t*Bu-$C_{13}H_6$—$SiMe_2$-N*t*Bu)Nd($\mu$-Cl)(THF)]$_2$ (5).

To a solution of *t*Bu$_2$-$C_{13}H_6$H—$SiMe_2$-NH*t*Bu (108 mg, 0.265 mmol) in diethylether (20 ml) at −10° C. was added under vigorous stirring two equiv. of *n*BuLi (0.33 mL of a 1.6 M solution in hexane, 0.530 mmol). The reaction mixture was allowed to warm to ambient temperature and stirred for 8 h. To the resulting orange solution of the dilithium salt in ether cooled to −20° C. was added a suspension of YCl$_3$ THF-adduct (prepared from 52.0 mg, 0.265 mmol of YCl$_3$) in ether (30 mL). The mixture was vigorously stirred and warmed to room temperature; the color turned yellow after 30-40 min. The yellow solution was decanted from precipitate, volatiles were removed in vacuo and the resulting residue was washed with pentane (2×20 mL) to give a yellow powder (101.2 mg). The $^1$H NMR spectrum of crude complex (2) shows the existence of two species in solution and gave the following results. (THF-$d_8$, 200 MHz, 25° C.): 1$^{st}$ product: δ 7.90 (d, 2H, $^4J_{HH}$=2.1 Hz, 4,5-H), 7.69(d,2H $^3J_{HH}$=8.6 Hz, 1,8-H), 6.90 (dd, 2H, $J_{HH}$=2.1, 8.6 Hz, 2,7-H), 1.36 (s, 18H, CCH$_3$ (Flu)), 1.20 (s, 9H, NCCH$_3$), 0.38 (s, 6H, SiCH$_3$); 2$^{nd}$ product: δ 7.83 (m, 2H, $^4J_{HH}$=2.1 Hz, 4,5-H), 7.54 (d, 2H, $^3J_{HH}$=8.6 Hz, 1,8-H), 6.84 (dd, 2H, $J_{HH}$+2.1, 8.6Hz, 2,7-H), 1.35 (s, 18H, CCH$_3$(Flu)), 1.11 (s, 9H, NCCH$_3$), 0.40 (s, 6H, SiCH$_3$). The crude product was recrystallized from Et$_2$O:THF:pentane (~0.5:1:3) to give yellow crystals (88.2 mg, 55%). The $^1$H NMR of recrystallized complex (2) is represented in FIG. 5 and gave the following results that show the presence of a sole species. (THF-$d_8$, 300 MHz, 25° C.): δ 7.94 (d, 2H, $^4J_{HH}$=1.8 Hz, 4,5-H), 7.72 (d, 2H, $^3J_{HH}$=8.3 Hz, 1,8-H), 7.13 (dd, 2H, $J_{HH}$=1.8, 8.3 Hz, 2,7-H), 1.43 (s, 9H, NCCH$_3$), 1.36 (s, 18H, CCH$_3$(Flu)), 0.27 (s, 6H, SiCH$_3$). The $^{13}$C NMR spectrum of complex (2) is represented in FIG. 6 and gave the following results. (THF-$d_8$, 75 MHz, 25° C.): δ 144.6, 137.8, 133.7, 121.1 (C-1,-8), 120.0 (C-2, -7), 115.5

(C-4,-5), 79.0 (C-9), 54.7 (NCCH$_3$), 36.9 (NCCH$_3$), 35.4 (Flu-CCH$_3$), 33.2 (Flu-CCH$_3$), 6.2 (SiCH$_3$).

Salt Metathesis Reaction between [3,6-di-*t*Bu-C$_{13}$H$_6$—SiMe$_2$-N*t*Bu]Li$_2$ and LaCl$_3$(THF)$_n$. Preparation of [{(*t*Bu$_2$-C$_{13}$H$_6$)—SiMe$_2$-N*t*Bu}$_2$La]$^-$[Li(THF)$_4$]$^+$ (3).

The same procedure than that described above was carried out from the LaCl$_3$ THF-adduct (prepared from 186 mg, 0.758 mmol of LaCl$_3$) and *t*Bu$_2$-C$_{13}$H$_6$H—SiMe$_2$-NH*t*Bu (310 mg, 0.760 mmol) to yield a yellow microcrystalline solid (440 mg). NMR of the crude complex showed the presence of two species in solution and gave the following results. $^1$H NMR (THF-d$_8$, 200 MHz, 25° C.): 1$^{st}$ product: δ 7.93 (d, 2H, $^4J_{HH}$=2.0 Hz, 4,5-H), 7.73 (dd, 2H, $J_{HH}$=0.5, 8.6 Hz, 1,8-H), 6.94 (dd, 2H, $J_{HH}$=2.1, 8.6 Hz, 2,7-H), 1.41 (S, 18H, CCH$_3$ (Flu)), 1.25 (s, 9H, NCCH$_3$), 0.43 (s, 6H, SiCH$_3$); 2$^{nd}$ product: δ 7.83 (m, 2H, $^4J_{HH}$=2.1 Hz, 4,5-H), 7.54 (d, 2H, $J_{HH}$=8.6 Hz, 1,8-H), 6.84 (dd, 2H, $J_{HH}$=2.1, 8.6 Hz, 2,7-H), 1.35 (s, 18H, CCH$_3$(Flu)), 1.16 (s, 9H, NCCH$_3$), 0.45 (s, 6H, SiCH$_3$). Recrystallization of the crude product from THF-pentane (~1:4) mixture gave pale-orange crystals (0.38 g, 77%). NMR of the recrystallized complex showed the presence of a sole species in solution and gave the following results. $^1$H NMR (FIG. 5.) (THF-d$_8$, 300 MHz, 25° C.): δ 7.82 (d, 2H, $^4J_{HH}$=1.8 Hz, 4,5-H), 7.53 (d, 2H, $^3J_{HH}$=8.2 Hz, 1,8-H), 6.84 (dd, 2H, $J_{HH}$=1.8, 8.2 Hz, 2,7-H), 1.35 (s, 18H, CCH$_3$(Flu)), 1.19 (s, 18H, NCCH$_3$), 0.39 (s, 6H, SiCH$_3$). $^{13}$C NMR (THF-d$_8$, 75 MHz, 25° C.): δ 144.4, 131.4, 127.7, 119.5 (C-1,-8), 118.5 (C-2, -7), 114.9 (C-4,-5), 84.4 (C-9), 50.7 (NCCH$_3$), 35.5 (Flu-CCH$_3$), 35.4 (NCCH$_3$), 34.1 (Flu-CCH$_3$), 6.9 (SiCH$_3$). Anal. Calcd for C$_{70}$H$_{110}$N$_2$O$_4$LiSi$_2$La: C, 67.49; H, 8.90; N, 2.25. Found: C, 67.31; H, 8.37; N, 2.40.

Synthesis of [{*t*Bu$_2$—C$_{13}$H$_6$—SiMe$_2$-N*t*Bu}$_2$La]$^-$[Li(Et$_2$O)$_2$]$^+$ (4).

To a solution of *t*Bu$_2$-C$_{13}$H$_6$H—SiMe$_2$—NH*t*Bu (340 mg, 0.834 mmol) in diethylether (30 mL) at −10° C. wa added under vigorous stirring two equiv. of $^n$BuLi (1.0 mL of a 1.6 M solution in hexane, 1.66 mmol). The reaction mixture was allowed to warm to ambient temperature and stirred for 8 h. To the resulting orange solution of the dilithium salt in ether cooled to −35° C. in glovebox was added a powder of LaCl$_3$(THF)$_{1.5}$ (295 mg, 0.834 mmol). The mixture was vigorously stirred and warmed to room temperature; the color turned orange-yellow after 20 min. The yellow solution was decanted from precipitate and concentrated in vacuo. Hexane (ca. 2-3 mL) was added to the ether solution and orange-yellow crystals started to grow to get in the next 10 h microcrystals of molecule (4) (0.30 g, 33%). $^1$H NMR (THF-d$_8$, 200 MHz, 60° C.): δ 7.79 (d, 4H, $^4J_{HH}$=2.0 Hz, 4,5-H), 7.25 (d, 4H, $J_{HH}$=8.4 Hz, 1,8-H), 7.00 (dd, 4H, $J_{HH}$=2.0, 8.4 Hz, 2,7-H), 3.36 (q, 8H, CH$_2$OCH$_3$), 1.51 (s, 18H, NCCH$_3$), 1.36 (s, 36H, CCH$_3$(Flu)), 1.08 (t, 12H, CH$_2$OCH$_3$), 0.17 (s, 12H, SiCH$_3$).

Synthesis of [{*t*Bu$_2$-Cl$_{13}$H$_6$—SiMe$_2$-N*t*Bu}Nd(μ-Cl)(THF)]$_2$ (5).

The same procedure as that described above was carried out from the NdCl$_3$ THF-adduct (prepared from 156 mg, 0.623 mmol of NdCl$_3$) and *t*Bu$_2$-C$_{13}$H$_6$H—SiMe$_2$-NH*t*Bu (255 mg, 0.623 mmol) to yield molecule (5) as a yellow microcrystalline solid (0.45 g, 77%). Crystallization of the reaction mixture from an Et$_2$O-hexane mixture gave green crystals of molecule (5) suitable for X-ray diffraction (0.15 g, 26%).

Reaction of [3,6-di-*t*Bu-C$_{13}$H$_6$—SiMe$_2$-N*t*Bu]Y(CH$_2$SiMe$_3$)(THF)$_2$ (1) with PhSiH$_3$ or H$_2$ to produce Y-hydride (6).

Method A. To a solution of [C$_{13}$H$_8$—SiMe$_2$-NtBu]Y(CH$_2$TMS)(THF)$_2$ (0.100 g, 0.137 mmol) in benzene (5 mL) was added phenylsilane (85 μL, 0.688 mmol) at 25° C. The mixture was stirred for 1 h at this temperature. The yellow precipitate formed was filtrated, washed with benzene (2 mL) and dried in vacuo to give 0.070 g of a pale-yellow microcrystalline product insoluble in THF and hydrocarbons. Method B. A solution of [C$_{13}$H$_8$—SiMe$_2$-NtBu]Y(CH$_2$TMS)(THF)$_2$ (0.125 g, 0.172 mmol) in benzene (5 mL) was exposed in hydrogene atmosphere (1 atm, 25° C.) for 12 hours to yield after similar workup 30 mg of a pale-yellow insoluble product.

Polymerization

Polymerisation of methyl methacrylate (MMA) and styrene have been carried out with complexes (1), (2) and (6). Complexes (1) and (2) were prepared as disclosed hereabove. Complex (6) is an Y-hydride complex. Complex (2) reacts smoothly with bulk MMA at room temperature and 50° C. to give atactic PMMA of narrow molecular weight distribution (MWD). The molecular weight distribution is defined by the polydispersion index D that is the ratio Mw/Mn of the weight average molecular weight Mw over the number average molecular weight Mn. Alkyl complex (1) initiates sluggishly polymerization of MMA and styrene. The polymerization results are displayed in Table I.

TABLE I

| Complex | Condit | Monomer | Temp. ° C. | Conv. % | M$_w$ 10$^3$ | MW D | Tacticity rr | Tacticity mr | Tacticity mm |
|---|---|---|---|---|---|---|---|---|---|
| 2 | Bulk | MMA | 25 | 26 | 250 | 2.85 | 26 | 40 | 34 |
| 2 | " | " | 50 | 65 | 216 | 3.60 | 21 | 40 | 39 |
| 1 | " | " | 25 | Traces | — | — | — | — | — |
| 1 | " | " | 50 | Traces | — | — | — | — | — |
| 1 | Toluene | " | 25 | 2 | not sol | — | 29 | 29 | 42 |
| 1 | Toluene | " | 50 | 2 | not sol | — | 32 | 29 | 40 |
| 6 | Toluene | " | 25 | 13 | 19 | 2.8 | 33 | 26 | 41 |
| 1 | Bulk | Styrene | 25 | Traces | — | — | — | — | — |
| 1 | " | " | 50 | 3 | 455 | 1.81 | | | |

Reaction conditions:
MMA/[metal] = 200-500,
t = 12 h.

The invention claimed is:

1. A metallocene catalyst component characterized by the formula:

[(Flu-SiR$_2$—N—R')$_2$M]$^-$[Q(L)$_p$]$^+$      (II)

wherein:
Flu is a substituted or unsubstituted fluorenyl group;
M is a metal in Group IIIB of the Periodic Table;
SiR$_2$ is a structural bridge between N and the 9 carbon atom of the fluorenyl group imparting stereorigidity to the component, wherein each R is the same or different and is an alkyl having from 1 to 20 carbon atoms;

R' is hydrogen or is characterized by the formula $ZR^\$_3$ wherein Z is C or Si and $R^\$$ is a hydrocarbyl group having from 1 to 20 carbon atoms;

L is a coordinating solvent;

Q is an alkali metal, an alkaline earth metal or a metal in Group IIIA of the Periodic Table; and p is from 2 to 4.

2. The metallocene catalyst component of claim 1 wherein M is yttrium, lanthanum or a member of the lanthanide series.

3. The metallocene catalyst component of claim 2 wherein M is yttrium, lanthanum or neodymium.

4. The metallocene catalyst component of claim 1 wherein Flu is a substituent fluorenyl group with at least one hydrocarbyl group having from 1 to 20 carbon atoms.

5. The metallocene catalyst of claim 1 wherein R' is characterized by the formula $ZR^\$_3$.

6. The metallocene catalyst component of claim 5 wherein $ZR^\$_3$ is a tert-butyl group.

7. The metallocene catatyst component of claim 1 wherein Q is selected from the group consisting of Li, Na, Mg and Al.

8. A process for preparing by a salt metathesis reaction the metallocene catalyst component of claim 1 comprising:

(a) suspending $MX_3(THF)_n$ in an ether, wherein X is a halogen;

(b) suspending a deprotonated dilithium salt [Flu-$SiR_2$—N—R']$Li_2$ in an ether;

(c) carrying out the salt metathesis reaction of suspensions (a) and (b) in an ether at a temperature within the range of −80° C. to 60° C.;

(d) recrystallizing the crude product obtained in (c) after evaporation of volatiles from an ether or a mixture of an ether and an hydrocarbon at a temperature of from −60° to −0° C.; and (e) retrieving a crystalline powder of formula (I) or formula (II).

9. A process for the polymerization of a monomer comprising:

(a) providing the metallocene catalyst eomponent of claim 1

(b) contacting said metallocene catalyst component with a monomer in a polymerization reaction zone under polymerization conditions to produce a polymer product by the polymerization of said monomer; and (c) recovering said polymer product from said polymerization reaction zone.

10. The method of claim 9 wherein said monomer is methyl methacrylate.

11. The method of claim 9 wherein said monomer is styrene.

* * * * *